United States Patent [19]

Longoria

[11] Plant 4,514

[45] Mar. 25, 1980

[54] PLANT OF THE ARACEAE FAMILY

[76] Inventor: Gilbert R. Longoria, P.O. Box 146, Mission, Tex. 78472

[21] Appl. No.: 5,147

[22] Filed: Jan. 22, 1979

[51] Int. Cl.[2] ..... A01H 5/00

[52] U.S. Cl. ..... Plt./88

[58] Field of Search ..... Plt./88

*Primary Examiner*—Robert E. Bagwill

*Assistant Examiner*—James R. Feyrer

*Attorney, Agent, or Firm*—Roger L. Martin

[57] ABSTRACT

A new plant variety of the Araceae family is related to *Syngonium podophyllum* xanthophilum but distinguishable therefrom in the juvenile stages by an achlorophyllous field in the variegated leaf and which in color is dominated by a pink, red, yellowish pink and/or reddish brown hue.

1 Drawing Figure

1

A new plant variety of the Araceae family has been named the *Syngonium podophyllum* 'Maya Red' by the inventor. The new variety was developed from a seedling that was derived from a seed taken from a plant specimen of the *Syngonium podophyllum* xanthophilum variety and which is commonly cultivated under the name of 'Green Gold'. The seedling was under cultivation in a nursery at Mission, Tex. at the time of the discovery and since then the new variety has been asexually reproduced at the same nursery by the propagation of stem cuttings taken from the specimen.

Plant specimens of the 'Green Gold' variety, in the juvenile stage, usually have arrow shaped leaves with a chlorophyllous field that is in part masked by an overlaying achlorophyllous field. This achlorophyllous field is, in color, dominated by a yellow green hue and the achlorophyllous field gradually disappears in subsequent growth stages of the plant specimens with the leaves in these subsequent growth stages become palmately lobed and parted and sometimes pedate. Specimens of the 'Maya Red' variety are similar to those of the 'Green Gold' variety in growth habit but are principally distinguishable by an overlaying achlorophyllous field in the juvenile stages that, in color, is dominated by pink, red, yellowish pink and/or reddish brown hues.

One object of the invention has been to develop a new variety of the Arcaceae family for the foliage plant market and which is distinguishable from the known varieties of this family. This object has been fully realized by the invention as will be apparent from the following plant description contained herein and where it will be seen that the new plant variety is mainly distinguishable from its antecedents and known related varieties by a growth habit providing specimens which have plant parts that, in size and shape, closely approach those of the 'Green Gold' variety but which are nevertheless distinguished in the juvenile stages by an overlaying achlorophyllous field that in color is dominated by pink, red, yellowish pink and/or reddish brown hues.

The accompanying drawings serve by color photographic means to illustrate the new variety, one sheet showing a single plant specimen of the new variety while the other sheet more closely illustrates the achlorophyllous field and its color in the juvenile stages.

The following is a detailed description of the new variety and is based on observations of well fertilized specimens which were grown in the Mission, Tex. area,

2 the description being further based on the observations of specimens during the months of July, August and September and which were 6–10 months old at the time of the observations.

Except where general terms of ordinary color significance are obviously used, color terminology and color designations reported herein are in accord with the ISCC-NBS System of Designating Colors as described in the United States Department of Commerce, National Bureau of Standards, Circular 553, entitled ISCC-NBS "Method of Designating Colors and Dictionary of Colored Terms" with the color designations having been derived through interpretation of Munsell Color Notations obtained by comparing plant specimens with the color specimens in the current "Neighboring Hues Edition" of the Munsell Book of Color, published by Munsell Color Company, Inc., of Baltimore, Md., and to which the reported notations (Munsell Hue, Munsell Value/Munsell Chroma) are referenced.

PLANT DESCRIPTION

Name: *Syngonium podophyllum* 'Maya Red'

Origin: Seedling.

Parentage:

A. *Maternal.*—*Syngonium podophyllum* xanthophilum variety commonly known as 'Green Gold'.

B. *Paternal.*—Unknown.

Classification:

A. *Botanic.*—1. Family: Araceae (Arum family). 2. Genus: Syngonium. 3. Species: *podophyllum.*

B. *Commercial.*—Foliage plant.

Form: Terrestrial, vining tropical herb.

Stems:

A. *General.*—Caulescent, vining, and cylindrical with aerial roots, and usually with a solitary leaf and a latent vegetative bud at each node.

B. *Texture.*—Glabrous and fleshy, and hardening with age.

C. *Shape.*—Generally terete to cylindrical and sometimes with a slight flattening of one surface on young portions of the stem.

D. *Size.*—1. Diameter: Usually between 3 mm to 9 mm. 2. Internode length: Usually between 15 mm and 250 mm.

E. *Color.*—Stem (vine) coloration usually varies both within the same stem and between different stems. Older portions of the stem are usually characterized by olive and/or olive green hues that are commonly grayish olive (7.5 Y 3/2) (10 Y 3/2), olive gray (10 Y 3/1), moderate olive green (2.5 GY 4/4) (5 GY 4/4), and/or grayish olive green (near 2.5 GY 3/2), the color pattern being variable, at times being continuous around the stem at other times being gradually grading from one hue to another and at yet other times having distinct, longitudinally oriented and circumferentially spaced apart streaks of differing colors. Younger portions of the stems are usually characterized by reddish orange, brown, and/or orange hues that are derived from chlorophyllous spots that are interspersed with spots containing light pigmentation (magnification 10×). Commonly grayish, grayish orange (near 2.5 YR 6/6), strong brown (near 2.5 YR 4/6), and/or moderate orange (near 5 YR 6/6).

Leaves:

A. *General.*—Simple, extipulate and petiolate.

B. *Arrangement.*—Alternate.

C. *Margins.*—Entire in early stages of plant growth and becoming palmately lobed and parted and sometimes pedate in later stages of plant growth.

D. *Venation.*—Palmate.

E. *Shape.*—1. Leaf apices: Acute and accuminate. 2. Leaf bases: Hastate in early stages of plant growth and becoming palmately lobed and parted and sometimes pedate in later stages of plant growth.

F. *Petioles.*—1. General: Fleshy, sheathing, and slightly ribbed. 2. Texture: Glabrous, fleshy, and ribbed. 3. Shape: Generally terete with a thinning taper from attachment at stem to attachment with leaf blade. The proximal petiole portion is stem sheathing with the distal petiole portion exhibiting an adaxial flattening. 4. Size: A. Diameter — Usually between 1.5 mm and 6 mm when measured midway between stem and leaf blade attachments to petiole in mature specimen. B. Length — usually between 4 cm and 30 cm in mature specimen. 5. Color: Commonly moderate olive green (near 5 GY 4/4) (7.5 GY 4/4), and/or moderate yellow green (near 5 GY 5/6) (near 7.5 GY 5/6) with the adaxial petiole side generally appearing "darker" than the abaxial side.

G. *Leaf blades.*—1. General: Thin, fleshy and variegated in early or juvenile growth stages of the plant. 2. Texture: A. Upper surface (adaxial) — Glabrous with most veins depressed. B. Lower surface (abaxial) — Glabrous with most veins raised. 3. Size: A. Length — Usually between 4 cm and 28 cm in mature specimens. B. Width (at widest point-basal area) — usually between 4 cm and 28 cm in mature specimens. 4. Color: A. Upper surface — variegated during juvenile or early plant growth stages with a basic chlorophyllous field that is in part masked by an overlying achlorophyllous field the achlorophyllous field commonly dominating the upper surface in the juvenile plant growth stages and receding to the vein areas and ultimately disappearing in later plant growth stages. The chlorophyllous field usually has a color that is dominated by olive green and/or yellowish green hues and the overlaying achlorophyllous field has a color which is dominated by a pink, red, yellowish pink, and/or yellowish brown hue in the juvenile stage and where a yellow green hue commonly appearing in stages subsequent to the juvenile stage. Commonly moderate olive green (7.5 GY 4/4) and/or dark yellowish green (near 10 GY 4/4) in the chlorophyllous field. Commonly moderate pink (2.5 R 7/6) (near 2.5 R 7/4) (near 5 R 7/4), dark pink (2.5 R 6/6), pale pink (near 5 R 8/2), grayish pink (near 5 R 8/2) (5 R 7/2), light grayish red (near 5 R 6/4) (7.5 R 6/4), pale yellowish pink (near 7.5 R 8/2) (near 10 R 8/2) (near 2.5 YR 8/2), grayish yellowish pink (near 7.5 R 8/2) (7.5 R 7/2) (near 10 R 8/2) (10 R 7/2) (2.5 YR 8/2) (2.5 YR 7/2) (near 5 YR 7/2), moderate yellowish pink (7.5 R 7/4), and/or light reddish brown (near 10 R 6/4) in the achlorophyllous field during the juvenile stages and with pale yellow green (near 10 Y 8/2) (2.5 GY 8/2) (near 5 GY 8/2) commonly appearing in the variegated areas in subsequent stages. B. Lower surface — commonly moderate yellow green (7.5 GY 5/4) (5 GY 5/4) (near 2.5 GY 6/4) (near 2.5 GY 7/4) (near 2.5 GY 7/6) and/or (5 GY 7/6).

H. *Inflorescence.*—No flowering has been noted to date.

The following is a description of an individual plant specimen.

Age of Specimen: 10 months from propagation of single node cutting.

Pot Size: 6".

Stem (vine):

A. Length.—130 cm.

B. *Number of nodes.*—14.

C. *Diameter.*—1. Basal: 5 mm. 2. Apical: 5 mm.

D. *Internode length.*—Varies from 28 mm to 205 mm.

E. *Color.*—Moderate olive green (2.5 GY 4/4) (5 GY 4/4) in proximal area and grayish reddish orange (near 2.5 YR 6/6) in distal area.

Leaves:

A. *Number of mature leaves.*—17.

B. *Number of developing leaves.*—4.

C. *Petioles.*—1. Length: From 55 mm to 205 mm. 2. Diameter (midway between stem and blade attachments): From 2 mm to 4 mm. 3. Color — moderate olive green (7.5 GY 4/4) on adaxial surface and moderate yellow green (near 7.5 GY 5/6) on abaxial surface.

D. *Leaf blades.*—1. Length — from 50 mm to 235 mm. 2. Width (at base) — from 72 mm to 215 mm. 3. Color — A. Upper surface: Moderate olive green (7.5 GY 4/4) in chlorophyllous field and dark pink (2.5 R 6/6), moderate pink (5 R 7/4), moderate yellowish pink (7.5 R 7/4), and light grayish red (7.5 R 6/4) in achlorophyllous field of juvenile stages. B. Lower surface: Moderate yellow green (7.5 GY 5/4) with moderate yellow green (5 GY 7/6) veins.

Infloresence: None.

I claim:

1. The new and distinct plant variety of the Araceae family substantially as shown and described herein.

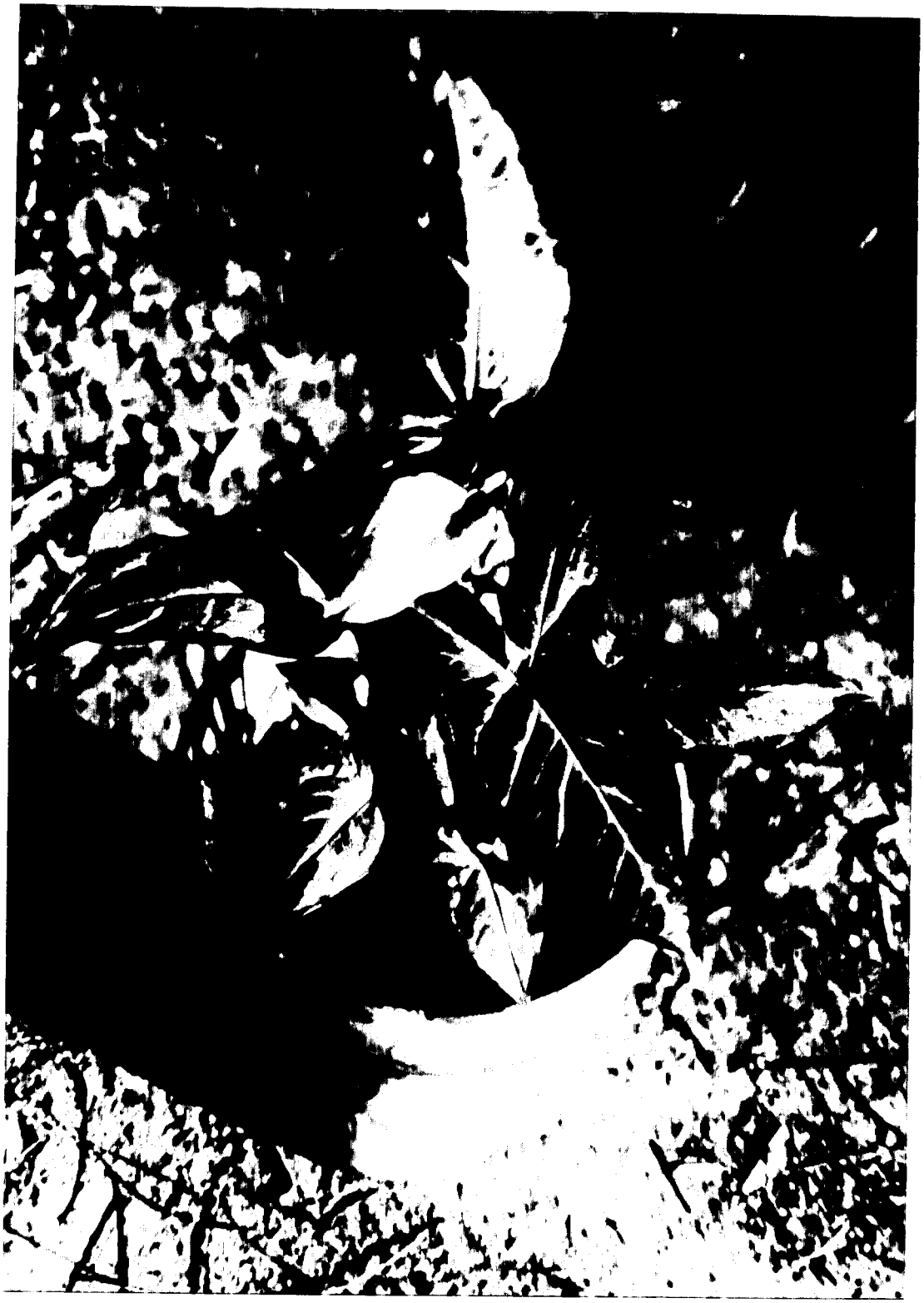

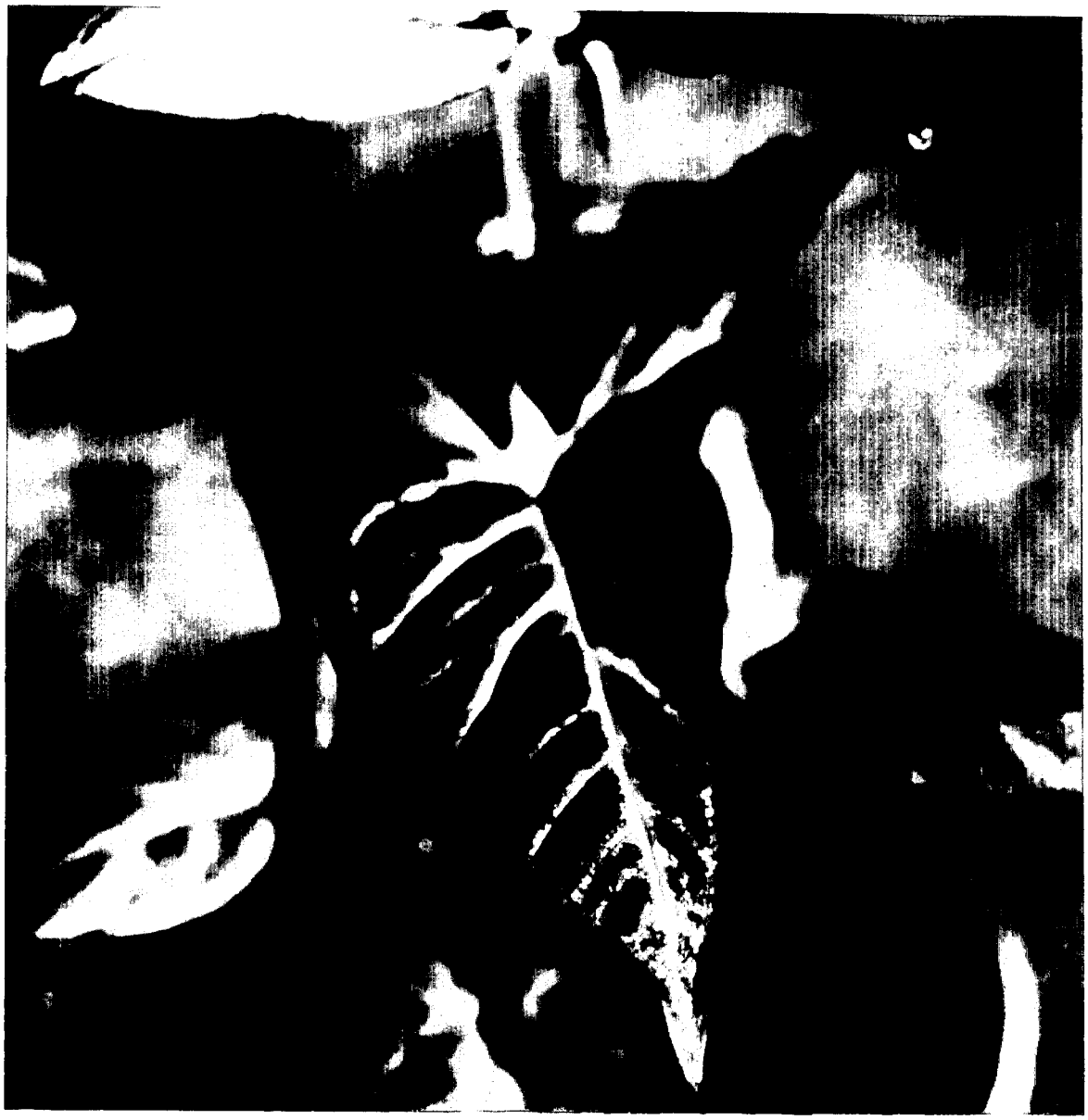

* * * * *